United States Patent [19]

Badmin et al.

[11] 4,182,772

[45] Jan. 8, 1980

[54] SYNERGISTIC COMBINATIONS OF AMITRAZ AND CERTAIN PYRETHROIDS

[75] Inventors: John S. Badmin, Isle of Sheppey; Robert J. Knight, Ashford, both of England

[73] Assignee: Shell Oil Company, Houston, Tex.

[21] Appl. No.: 932,889

[22] Filed: Aug. 10, 1978

[30] Foreign Application Priority Data

Aug. 10, 1977 [GB] United Kingdom ............... 33524/77

[51] Int. Cl.$^2$ ............................................. A01N 9/02
[52] U.S. Cl. ...................... 424/304; 424/330
[58] Field of Search ................................ 424/304, 330

[56] References Cited

U.S. PATENT DOCUMENTS 3,996,244  12/1976  Fujimoto et al. ..................... 424/282

OTHER PUBLICATIONS

Chemical Abstracts, vol. 84 (1976) p. 70358f.

*Primary Examiner*—V. D. Turner

[57] ABSTRACT

A pesticidal composition comprising as essential ingredients N,N-di-(2,4-xylyliminomethyl)methylamine, commonly known as amitraz, and at least one of certain pesticidally active pyrethroid compounds.

5 Claims, No Drawings

SYNERGISTIC COMBINATIONS OF AMITRAZ AND CERTAIN PYRETHROIDS

BACKGROUND OF THE INVENTION

Certain cyclopropane carboxylic acid derivatives are a useful class of pesticides called "pyrethroids", which have been of considerable interest because of their quick knockdown activity, low persistence as toxic residues and their low mammalian toxicity. Certain derivatives of phenylacetic acids have also been found to have properties of the pyrethroid type. Of particular interest are certain α-cyanobenzyl phenylacetate pyrethroids. Unfortunately, while such compounds are desirable pesticides, they tend to be difficult or expensive to manufacture due to their relatively complex chemical structures. It is thus desirable to minimize the amount of the pyrethroid that is required to control the pests.

DESCRIPTION OF THE INVENTION

It has been found that combinations of such α-cyanobenzyl phenylacetate pyrethroids and amitraz (N,N-di-(2,4-xylyliminomethyl)-methylamine), as hereinafter described, possess synergistic activity with respect to acarid pests—that is to say, the combinations exhibit more pesticidal activity than would be expected from the activities of the two pesticide components, each considered above.

The contemplated pyrethroids are those described by the general formula:

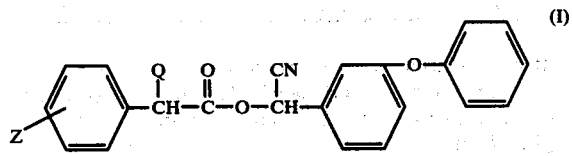

wherein Z represents a halogen atom having an atomic number of from 9 to 35, inclusive, preferably a chlorine atom, or an alkoxy group of 1 to 4 carbon atoms, e.g., methoxy, Q represents an alkyl group of 1 to 6 carbon atoms, especially a branched chain group, such as an isopropyl group.

A preferred pyrethroid of this class is α-cyano-3-phenoxybenzyl α-isopropyl-4-chlorophenyl acetate, designated as Compound Y, in the Examples given hereinafter.

It should be noted that the compounds of formula I can exist in the form of cis-trans isomers, and/or optical isomers. This invention contemplates each of the pesticidally active isomers, as well as racemic mixtures, and other mixtures of isomers of one or more of the pesticidally active compounds according to formula I. The various isomers of the compounds according to formula I may have different pesticidal activities and/or knockdown potency. Accordingly, one may prefer to resolve mixtures of isomers to recover a more pesticidally active isomer or racemic mixture or to prepare the more active forms directly, and use it or them in the compositions of the invention.

Combinations of amitraz with one or more of the contemplated pyrethroids not only have a markedly wider spectrum of activity than the pyrethroid or the amitraz alone, but also produce a surprising synergistic effect with respect to acarids, such as for example, glasshouse red spider mites, *Tetranychus urticae*. The combinations also possess useful properties with respect to the eggs of lepidopterous and acarine pests; they have uses in the agrochemical and animal health fields.

Suitably, the weight ratio of the pyrethroid to amitraz lies within the range of from about 5:1 to about 1:50, and particularly within the range of from about 1:1 to about 5:1.

Pesticidal compositions according to the invention preferably also employ a carrier, a surface-active agent or both a carrier and a surface-active agent, to facilitate application of the composition to the pest or its habitat at the desired dosage rates.

The term "carrier" as used herein means a solid or fluid material, which may be inorganic or organic and of synthetic or natural origin.

Typical solid carriers include natural and synthetic clays and silicates, for example natural silicas, such as diatomaceous earths and aluminum silicates, for example, kaolinites, montmorillonites, and micas. Typical fluid carriers are ketones, for example, methylcyclohexanone, aromatic hydrocarbons, for example, methylnaphthalenes, petroleum fractions, such as, for example, petroleum xylenes and light mineral oils, and chlorinated hydrocarbons, for example carbon tetrachloride. Mixtures of liquids are often suitable.

One or more surface-active agents and/or stickers can be included in the formulation. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol, condensates of these with ethylene oxide and/or propylene oxide; condensation products of fatty alcohols or alkyl phenols, for example poctylphenol or p-octylcresol, with ethylene oxide and/or propylene oxide; sulphates or sulphonates of these condensation products, alkali or alkaline earth metal salts, preferably sodium salts, or sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates, such as sodium dodecylbenzene sulphonate; and polymers of ethylene oxide and copolymers of ethylene oxide and propylene oxide.

The composition of the invention may for example be formulated as a wettable powder, microcapsules, a dust, granules, a solution, an emulsifiable concentrate, an emulsion, a suspension concentrate or an aerosol. The composition may have controlled release properties, or may be suitable for use as a bait.

Wettable powders usually contain 25, 50 or 75%w of active ingredient and may contain, in addition to inert solid material, 3–10%w of a dispersing agent and, where necessary, 0–10%w of a stabilizer, a penetrant and/or a sticker. A dust is usually formulated as a dust concentrate having a composition similar to that of a wettable powder but without a dispersant, and is diluted in the field with further solid carrier to give a composition usually containing ½–10%w of active ingredient.

Granules usually have a size in the range of from 10 to 100 BS mesh (1.676–0.152 mm) and may be manufactured by agglomeration or impregnation techniques.

Generally, granules will contain ½–25%w active ingredient and 0–10%w of additives, for example a stabilizer, slow-release modifier and/or a binding agent.

Emulsifiable concentrates usually contain, in addition to a solvent, and, when necessary, co-solvent, 10–50%w/v active ingredient, 2–20%w/v emulsifier and 0–20%w/v of other additives, for example a stabilizer, a penetrant and/or a corrosion inhibitor. A suspension concentrate is a stable, non-sedimenting, flowable product and usually contains 10–75%w active ingredient, 0.5–15%w of dispersing agent, 0.1–10%w of suspending agent, for example protective colloid and for a thixotropic agent, and 0–10%w of other additives including, for example, a defoamer, a corrosion inhibitor, a stabilizer, a penetrant and/or a sticker, and as dispersant, water or an organic liquid in which the active ingredient is substantially insoluble; certain organic additives and/or inorganic salts may be dissolved in the dispersant to assist in preventing sedimentation or as anti-freeze for water.

The aqueous dispersions and emulsions formed by diluting a wettable powder or an emulsifiable concentrate of the invention with water, also lie within the scope of the present invention. Such dispersions and emulsions may be of the water-in-oil or of the oil-in-water type, and may have a thick "mayonaise"-like consistency.

A composition of the invention may also contain other ingredients, for example, one or more other compounds possessing pesticidal, herbicidal or fungicidal properties, or attractants, for example pheromones or food ingredients, for use in baits and trap formulations.

The invention also includes a method of combating pests at a locus characterized in that a pesticidal composition according to the invention is applied to the locus.

The invention is further illustrated by the following Example, in which the joint action of two pesticides was analyzed according to the method of Yun-Pei Sun and E. R. Johnson, Journal of Economic Entomology, 1960, Volume 53, No. 5, pages 887-892.

Thus, the joint action of two pesticides was analyzed by determining the actual toxicity indices of the components and of mixtures of the compounds by reference to dosage-mortality curves. The theoretical toxicity of the mixture is equal to the sum over both components of the percentage of each individual compound multiplied by its respective toxicity index. Therefore, the joint toxicity or co-toxicity coefficient of a mixture $$= \frac{\text{Actual toxicity index of a mixture}}{\text{Theoretical toxicity index of a mixture}} \times 100$$

A coefficient of a mixture near 100 indicates probability of similar action by the two pesticides; independent action usually should give a coefficient less than 100, while a coefficient significantly above 100 strongly indicates synergism.

The compounds tested in the Example were amitraz and Compound Y.

EXAMPLE

Activity of Compound Y/Amitraz Combinations Against Tetranychus Urticae (glasshouse red spider mite)

The acaricidal activities of amitraz, compound Y and their mixtures was assessed by the following method.

The compounds and mixtures were formulated as solutions or suspensions in water containing 20% by weight of acetone and 0.05% by weight of Triton X-100 as wetting agent. The formulations contained 0.4% by weight of the compound or mixture to be tested and were diluted to produce formulations containing various concentrations. Leaf discs cut from French bean plants were sprayed with the formulations and left for ½ to 1 hour drying period. Each leaf disc was then inoculated with 10 red spider mites and mortality counts made 24 hours after inoculation. From these results the $LC_{50}$'s (the concentration by weight of active material in the spray required to kill 50% of the mite population) could be calculated.

The toxicity indices of the compounds and the mixtures were calculated using the following formula:

Toxicity Index =

$$\frac{LC_{50} \text{ of standard insecticide (Parathion) tested simultaneously}}{LC_{50} \text{ of test compound or mixture}}$$

The coefficient of cotoxicities were then calculated according to the method described above. The results are shown in the following Table.

TABLE

Activity of Pyrethroid Mixtures Against the Glasshouse Red Spider Mite (*Tetranychus urticae*)

| Treatment | Replicates | | Coefficient of Co-toxicity Replicates | |
|---|---|---|---|---|
| | 1 | 2 | 1 | 2 |
| Amitraz | 0.12 | 0.14 | — | — |
| Compound Y | 0.40 | 0.36 | — | — |
| Compound Y + Amitraz (2:1 ratio) | 0.17 | 0.17 | 133 | 141 |

It will be seen that the coefficients of cotoxicity are both in excess of 100 and clearly demonstrate the synergistic effect of the amitraz/pyrethroid combination.

We claim:
1. A pesticidal composition comprising as active ingredients:
   (a) N,N-di-(2,4-xylyliminomethyl)methylamine
   (b) an acaricidally active α-cyanobenzyl phenylacetate compound having the formula

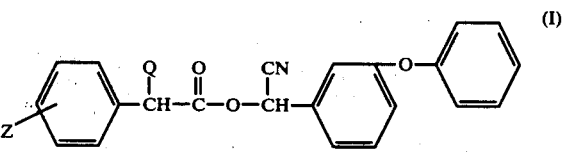

in which Z is a halogen atom having an atomic number of from 9 to 35, inclusive, or an alkoxy group containing from 1 to 4 carbon atoms and Q is an alkyl group containing from 1 to 6 carbon atoms, wherein the ratio of (a):(b) is from 1:1 to 5:1.

2. A composition according to claim 1 wherein in the compound of formula I, Z is a chlorine atom or a methoxy group, and Q is isopropyl.

3. A composition according to claim 2 for combating acarid pests wherein (b) is α-cyano-3-phenoxybenzyl α-isopropyl-4-chlorophenylacetate.

4. A method for combating acarid pests which comprises applying to the pests or to a locus an acaricidally effective amount of a composition according to claim 1.

5. A method according to claim 4 wherein b) is α-cyano-3-phenoxybenzyl α-isopropyl-p-chlorophenylacetate.

* * * * *